(12) United States Patent
Nakazato et al.

(10) Patent No.: US 6,187,781 B1
(45) Date of Patent: Feb. 13, 2001

(54) 4-TETRAHYDROPYRIDYLPYRIMIDINE DERIVATIVES

(75) Inventors: Atsuro Nakazato; Toshihito Kumagai; Taketoshi Okubo; Izumi Aibe; Hideo Tanaka; Shigeyuki Chaki; Shigeru Okuyama; Kazuyuki Tomisawa, all of Tokyo (JP)

(73) Assignee: Taisho Pharmaceutical Co., Ltd. (JP)

( * ) Notice: Under 35 U.S.C. 154(b), the term of this patent shall be extended for 0 days.

(21) Appl. No.: 09/381,462

(22) PCT Filed: Mar. 25, 1998

(86) PCT No.: PCT/JP99/01330
§ 371 Date: Sep. 21, 1999
§ 102(e) Date: Sep. 21, 1999

(87) PCT Pub. No.: WO98/42699
PCT Pub. Date: Oct. 1, 1998

(30) Foreign Application Priority Data

Mar. 26, 1997 (JP) .................................................. 9-072899
Dec. 9, 1997 (JP) .................................................. 9-338439

(51) Int. Cl.[7] .................... C07D 401/44; A61K 31/506; A61P 25/08
(52) U.S. Cl. .......................................... 514/275; 544/324
(58) Field of Search ..................... 544/324, 275

(56) References Cited

U.S. PATENT DOCUMENTS

| | | | |
|---|---|---|---|
| 5,705,646 | 1/1998 | Bright et al. | 546/144 |
| 5,712,303 | 1/1998 | Faraci et al. | 514/407 |
| 5,750,531 | * 5/1998 | Lee et al. | 514/256 |

FOREIGN PATENT DOCUMENTS

| | | |
|---|---|---|
| 7509725 | 10/1995 | (JP) . |
| 8500121 | 1/1996 | (JP) . |
| 9533727 | 4/1995 | (WO) . |
| 9533750 | 6/1995 | (WO) . |

OTHER PUBLICATIONS

Annual Reports in Medicinal Chemistry, vol. 30, James Bristol, ed., Academic Press, San Diego, 1995, p 21–30.*

* cited by examiner

Primary Examiner—Mark L. Berch
Assistant Examiner—Thomas McKenzie
(74) Attorney, Agent, or Firm—Lorusso & Loud

(57) ABSTRACT

A 4-tetrahydropyridylpyrimidine compound represented by formula (I):

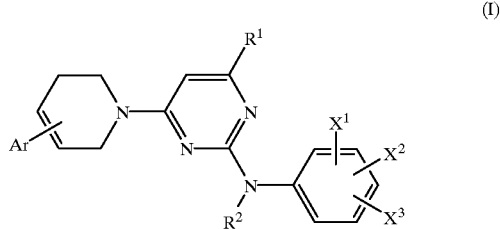

wherein Ar represents a phenyl group substituted with 1 to 3 substituents selected from a halogen atom, an alkyl group having 1 to 5 carbon atoms, an alkoxy group having 1 to 5 carbon atoms, and a trifluoromethyl group, a phenyl group, a thienyl group or a furanyl group; $R^1$ represents a hydrogen atom, an alkyl group having 1 to 5 carbon atoms, an amino group or an amino group substituted with 1 or 2 alkyl groups having 1 to 5 carbon atoms; $R^2$ represents an alkyl group having 1 to 5 carbon atoms, a cycloalkylalkyl group having 4 to 7 carbon atoms, an alkenyl group having 2 to 5 carbon atoms or an alkynyl group having 2 to 5 carbon atoms; and $X^1$, $X^2$, and $X^3$, which may be the same or different, each represent a hydrogen atom, a halogen atom, an alkyl group having 1 to 5 carbon atoms, an alkoxy group having 1 to 5 carbon atoms, an alkylthio group having 1 to 5 carbon atoms, an amino group or an amino group substituted with 1 or 2 alkyl groups having 1 to 5 carbon atoms, or a pharmaceutically acceptable salt thereof. The 4-Tetrahydropyridylpyrimidine compound finds utility in the treatment of diseases in which CRF is implicated.

6 Claims, No Drawings

4-TETRAHYDROPYRIDYLPYRIMIDINE DERIVATIVES

TECHNICAL FIELD

This invention relates to a treating agent for diseases which corticotropin releasing factor (CRF) is considered to take part in, such as depression, anxiety, Alzheimer's disease, Parkinson's syndrome, Huntington's chorea, eating disorders, hypertension, digestive diseases, drug dependence, cerebral infarction, cerebral ischemia, cerebral edema, head wounds, inflammation, and immunity-associated diseases.

BACKGROUND ART

CRF is a hormone composed of 41 amino acids (see *Science*, vol. 213, pp. 1394–1397 (1981), *J. Neurosci.*, vol. 7, pp. 88–100 (1987)). It has been suggested that CRF plays a key role in biological reactions to stress (see *Cell. Mol. Neurobiol.*, vol. 14, pp. 579–588 (1994), *Endocrinol.*, vol. 132, pp. 723–728 (1994), and *Neuroendocrinol.*, vol. 61, pp. 445–452 (1995)). CRF functions through two routes; a route through the hypothalamo-hypophysial-adrenal system for acting on the peripheral immune system and the sympathetic nervous system, and a route through the central nervous system in which it functions as a neurotransmitter (see *Corticotropin Releasing Factor: Basic and Clinical Studies of a Neuropeptide*, pp. 29–52 (1990)) CRF intracerebroventicularly administered to hypophysectomized rats and normal rats induces anxiety-like symptoms in both rats (see *Pharmacol. Rev.*, vol. 43, pp. 425–473 (1991) and *Brain Res. Rev.*, vol. 15, pp. 71–100 (1990)). That is, CRF is believed to participate in the hypothalamo-hypophysial-adrenal system and to function as a neurotransmitter in the CNS.

As Owens and Nemeroff collected in *Pharmacol. Rev.*, vol. 43, pp. 425–474 (1991), diseases in which CRF takes part include depression, anxiety, Alzheimer's disease, Parkinson's syndrome, Huntington's chorea, eating disorders, hypertension, digestive diseases, drug dependence, inflammation, and immunity-associated diseases. It has recently been reported that CRF is also involved in epilepsy, cerebral infarction, cerebral ischemia, cerebral edema, and head wounds (see *Brain Res.*, vol. 545, pp. 339–342 (1991), *Ann. Neurol.*, vol. 31, pp. 48–498 (1992), *Dev. Brain Res.*, vol. 91, pp. 245–251 (1996), and *Brain Res.*, vol. 744, pp. 166–170 (1997)). Therefore, an antagonist against a CRF receptor is useful as a treating agent for these diseases.

An object of the invention is to provide a CRF receptor antagonist effective as a treating agent or a prophylactic agent for diseases in which CRF is said to participate, such as depression, anxiety, Alzheimer's disease, Parkinson's syndrome, Huntington's chorea, eating disorders, hypertension, digestive diseases, drug dependence, epilepsy, cerebral infarction, cerebral ischemia, cerebral edema, head wounds, inflammation, and immunity-associated diseases.

DISCLOSURE OF THE INVENTION

As a result of extensive study on 4-tetrahydropyridylpyrimidine derivatives, the inventors have found that 4-tetrahydropyridylpyrimidine derivatives exhibits high affinity to a CRF receptor, thus completing the present invention.

The invention will be described hereinafter.

The invention relates to a 4-tetrahydropyridylpyrimidine derivative represented by formula (I):

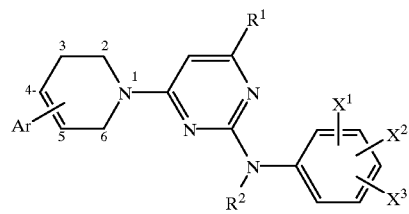

wherein Ar represents a phenyl group substituted with 1 to 3 substituents selected from a halogen atom, an alkyl group having 1 to 5 carbon atoms, an alkoxy group having 1 to 5 carbon atoms, and a trifluoromethyl group, a phenyl group, a thienyl group or a furanyl group; $R^1$ represents a hydrogen atom, an alkyl group having 1 to 5 carbon atoms, an amino group or an amino group substituted with 1 or 2 alkyl groups having 1 to 5 carbon atoms; $R^2$ represents an alkyl group having 1 to 5 carbon atoms, a cycloalkylalkyl group having 4 to 7 carbon atoms, an alkenyl group having 2 to 5 carbon atoms or an alkynyl group having 2 to 5 carbon atoms; and $X^1$, $X^2$, and $X^3$, which may be the same or different, each represent a hydrogen atom, a halogen atom, an alkyl group having 1 to 5 carbon atoms, an alkoxy group having 1 to 5 carbon atoms, an alkylthio group having 1 to 5 carbon atoms, an amino group or an amino group substituted with 1 or 2 alkyl groups having 1 to 5 carbon atoms, or a pharmaceutically acceptable salt thereof.

In the invention, Ar substitutes the tetrahydropyridine ring at the 4- or 5-position. The phenyl group substituted with 1 to 3 substituents selected from a halogen atom, an alkyl group having 1 to 5 carbon atoms, an alkoxy group having 1 to 5 carbon atoms, and a trifluoromethyl group includes a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-methylphenyl group, a 3-methylphenyl group, a 4-methylphenyl group, a 2-methoxyphenyl group, a 3-methoxyphenyl group, a 4-methoxyphenyl group, a 3,4-difluorophenyl group, a 3,5-difluorophenyl group, a 2,4-difluorophenyl group, a 3,4-dichlorophenyl group, a 3,5-dichlorophenyl group, and a 3-trifluoromethylphenyl group. The alkyl group having 1 to 5 carbon atoms is a straight-chain or branched alkyl group, such as a methyl group, an ethyl group, a propyl group, an isopropyl group, a butyl group, an isobutyl group, a pentyl group, and an isopentyl group. The cycloalkylalkyl group having 4 to 7 carbon atoms includes a cyclopropylmethyl group, a cyclopropylethyl group, and a cyclopropylpropyl group. The amino group substituted with 1 or 2 alkyl groups having 1 to 5 carbon atoms includes a methylamino group, a dimethylamino group, an ethylamino group, a diethylamino group, a propylamino group, a dipropylamino group, and an isopropylamino group. The alkynyl group having 2 to 5 carbon atoms includes a straight-chain or branched alkynyl group, such as a propargyl group and a 2-butynyl group. The halogen atom is a fluorine atom, a chlorine atom, a bromine atom or an iodine atom. The alkoxy group having 1 to 5 carbon atoms includes a straight-chain or branched alkoxy group, such as a methoxy group, an ethoxy group, a propoxy group, an isopropoxy group, a butoxy group, an isobutoxy group, a pentyloxy group, and an isopentyloxy group. The alkylthio group having 1 to 5 carbon atoms includes a straight-chain or branched alkylthio group, such as a methylthio group, an ethylthio group, a propylthio group, an isopropylthio group, a butylthio group, an isobutylthio group, a pentylthio group, and an isopentylthio group.

The pharmaceutically acceptable salt according to the invention includes salts with mineral acids, such as sulfuric acid, hydrochloric acid, and phosphoric acid; and those with organic acids, such as acetic acid, oxalic acid, lactic acid, tartaric acid, fumaric acid, maleic acid, citric acid, benzenesulfonic acid, and methanesulfonic acid.

In formula (I), $R^1$ is preferably a methyl group; $R^2$ is preferably an ethyl group, a cyclopropylmethyl group, an allyl group or a propargyl group; $X^1$ is preferably a hydrogen atom; $X^2$ is preferably a halogen atom or a methylthio group bonded at the 2-position of the benzene ring; and $X^3$ is preferably an isopropyl group or a dimethylamino group bonded at the 4-position of the benzene ring. Where Ar is at the 4-position of the tetrahydropyridine ring, it is preferably a phenyl group substituted with one halogen atom. Where Ar is at the 5-position, it is preferably a phenyl group having an alkyl group having 1 to 5 carbon atoms at the 2-position thereof.

The compound of formula (I) can be prepared in accordance with the following processes. In the reaction formulae shown below, Ar, $R^1$, $R^2$, $X^1$, $X^2$, and $X^3$ are as defined above; $R^3$ represents a hydrogen atom or $R^2$; $R^4$ and $R^5$, which may be the same or different, each represent an alkyl group having 1 to 5 carbon atoms, or they are connected to each other to form a 1,2-ethylenedioxy group or a 1,3-propylenedioxy group together with the respective adjacent oxygen atoms, $R^4O$ and $R^5O$ being bonded to the same carbon atom at the 3- or 4-position; $X^4$ represents a chlorine atom, a bromine atom or an iodine atom; $X^5$ represents a hydrogen atom, a chlorine atom, a bromine atom or an iodine atom; and Y represents an acyl group (e.g., an acetyl group or a benzoyl group), an alkoxycarbonyl group (e.g., an ethoxycarbonyl group or a t-butoxycarbonyl group), an alkyl group having 1 to 5 carbon atoms, or a benzyl group.

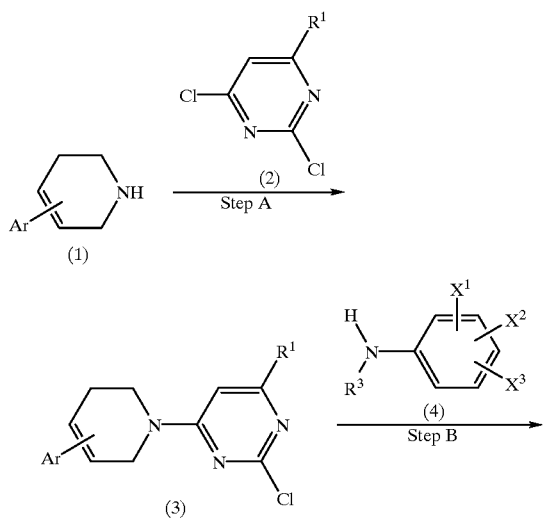

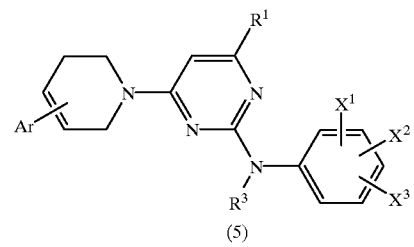

Step A:

A 1,2,3,6-tetrahydropyridine compound (1) and a 2,4-dichloropyrimidine compound (2) are allowed to react in an inert solvent in the presence of a base to form a compound of formula (3). Useful bases include amines, such as triethylamine, diisopropylethylamine, and pyridine; inorganic bases, such as sodium carbonate, potassium carbonate, sodium hydrogencarbonate, potassium hydrogencarbonate, sodium hydroxide, and sodium hydride; alcoholates, such as sodium methoxide, sodium ethoxide, and potassium t-butoxide; and metal amides, such as sodium amide and lithium diisopropylamide. Useful inert solvents include alcohols, such as methanol, ethanol, isopropyl alcohol, and ethylene glycol; ethers, such as diethyl ether, tetrahydrofuran, dioxane, and 1,2-dimethoxyethane; hydrocarbons, such as benzene and toluene; amides, such as N,N-dimethylformamide; acetonitrile, water; and mixtures thereof.

Step B:

The compound of formula (3) reacts with an aniline compound (4) in an inert solvent in the presence or absence of a base to give a compound (5) of the invention. Useful bases include amines, such as triethylamine, diisopropylethylamine, and pyridine; inorganic bases, such as sodium carbonate, potassium carbonate, sodium hydrogencarbonate, potassium hydrogencarbonate, sodium hydroxide, and sodium hydride; alcoholates, such as sodium methoxide, sodium ethoxide, and potassium t-butoxide; and metal amides, such as sodium amide and lithium diisopropylamide. Useful inert solvents include alcohols, such as methanol, ethanol, isopropyl alcohol, and ethylene glycol; ethers, such as diethyl ether, tetrahydrofuran, dioxane, and 1,2-dimethoxyethane; hydrocarbons, such as benzene, toluene, and xylene; amides, such as N,N-dimethylformamide; and dimethyl sulfoxide.

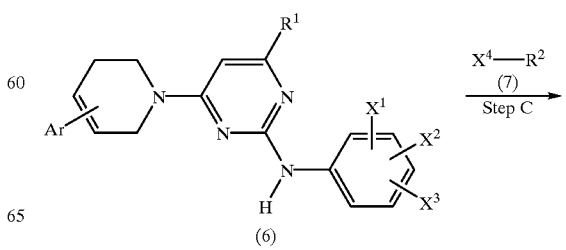

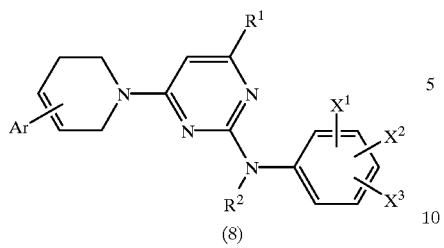

(8)

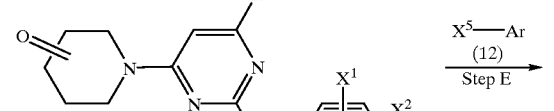

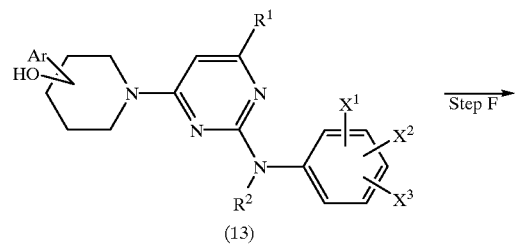

(11)

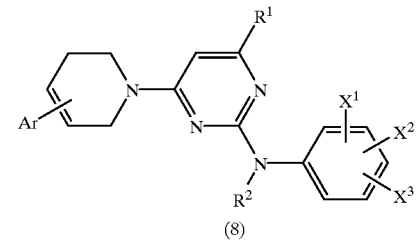

(13)

Step C:

A compound (6), which is the compound (5) wherein $R^3$ is a hydrogen atom, is led to a compound (8) of the invention by reaction with a halide (7) in an inert solvent in the presence of a base. Useful bases include amines, such as triethylamine, diisopropylethylamine, and pyridine; inorganic bases, such as sodium carbonate, potassium carbonate, sodium hydrogencarbonate, potassium hydrogencarbonate, sodium hydroxide, and sodium hydride; alcoholates, such as sodium methoxide, sodium ethoxide, and potassium t-butoxide; and metal amides, such as sodium amide and lithium diisopropylamide. Useful inert solvents include alcohols, such as methanol, ethanol, isopropyl alcohol, and ethylene glycol; ethers, such as diethyl ether, tetrahydrofuran, dioxane, and 1,2-dimethoxyethane; hydrocarbons, such as benzene, toluene, and xylene; amides, such as N,N-dimethylformamide; dimethyl sulfoxide, acetonitrile, water; and mixtures thereof.

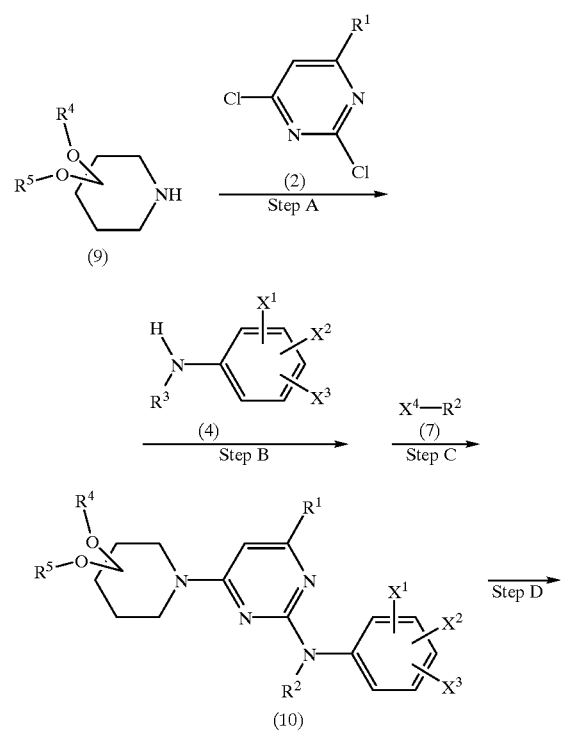

Process 3

The compound of the invention can also be obtained by starting with a compound represented by formula (9). That is, the compound represented by formula (9) and a 2,4-dichloropyrimidine compound (2) are subjected to step A followed by step B and, where $R^3$ is a hydrogen atom, further followed by step C to obtain a ketal compound (10).

Step D:

The ketal compound (10) is treated with an acid in an inert solvent to give a ketone compound (11). The inert solvent includes alcohols, such as methanol, ethanol, isopropyl alcohol, and ethylene glycol; ethers, such as diethyl ether, tetrahydrofuran, dioxane, and 1,2-dimethoxyethane; hydrocarbons, such as benzene, toluene, and xylene; ketones, such as acetone and methyl ethyl ketone; amides, such as N,N-dimethylformamide; water; and mixtures thereof. The acid includes inorganic acids, such as hydrochloric acid, hydrobromic acid, and sulfuric acid, and organic acids, such as p-toluenesulfonic acid, methanesulfonic acid, and trifluoroacetic acid.

Step E:

The ketone compound (11) and a metal compound, which is obtained from the compound of formula (12) and a metal reagent, are allowed to react in an inert solvent to obtain an alcohol compound (13). The metal reagent includes metals, such as magnesium and lithium, and organolithium compounds, such as n-butyl lithium, t-butyl lithium, phenyl lithium, lithium diisopropylamide, and lithium bis (trimethylsilyl)amide. The inert solvent includes ethers, such as diethyl ether, tetrahydrofuran, dioxane, and 1,2-dimethoxyethane, and hydrocarbons, such as hexane, benzene, toluene, and xylene.

Step F:

The alcohol compound (13) is led to a compound (8) of the invention by dehydration under an acidic condition or by conversion to an active species which is then subjected to reaction under a basic condition. The dehydration under an acidic condition is carried out in an inert solvent, such as an alcohol, e.g., methanol, ethanol, isopropyl alcohol or ethylene glycol; an ether, e.g., diethyl ether, tetrahydrofuran, dioxane or 1,2-dimethoxyethane; a ketone, e.g., acetone or methyl ethyl ketone; water; or a mixed solvent thereof, using an acid, such as an inorganic acid, e.g., hydrochloric acid, hydrobromic acid or sulfuric acid; a hydrogen halide, such as hydrogen chloride or hydrogen bromide; or an organic acid, such as p-toluenesulfonic acid, methanesulfonic acid, trifluoroacetic acid or formic acid. The term "active species" means the alcohol compound (13) with its hydroxyl group sulfonylated or acylated or the alcohol compound (13) with its hydroxyl group substituted with a halogen atom. Such an active species is obtained by allowing the alcohol compound (13) to react with a sulfonyl chloride (e.g., methanesulfonyl chloride or p-toluenesulfonyl chloride), an organic carbonyl chloride (e.g., acetyl chloride), an organic carboxylic acid anhydride (e.g., acetic anhydride or trifluoroacetic anhydride), a halogenating agent (e.g., sulfonyl chloride or phosphoryl chloride), and the like in an inert solvent in the presence of a base. Useful inert solvents include ethers, such as diethyl ether, tetrahydrofuran, dioxane, and 1,2-dimethoxyethane; hydrocarbons, such as benzene, toluene, and xylene; halides, such as chloroform and dichloromethane; and amides, such as N,N-dimethylformamide. Useful bases include amines, such as triethylamine, diisopropylethylamine, pyridine, and 4-dimethylaminopyridine; inorganic bases, such as sodium carbonate, potassium carbonate, sodium hydrogencarbonate, potassium hydrogencarbonate, sodium hydroxide, and sodium hydride; and metal amides, such as sodium amide and lithium diisopropylamide. The reaction under a basic condition is a reaction between the active species of the alcohol compound (13) and a base in an inert solvent. Useful inert solvents include ethers, such as diethyl ether, tetrahydrofuran, dioxane, and 1,2-dimethoxyethane; hydrocarbons, such as benzene, toluene, and xylene; halides, such as chloroform and dichloromethane; and amides, such as N,N-dimethylformamide. Useful bases include amines, such as triethylamine, diisopropylethylamine, pyridine, and 1,8-diazabicyclo[5.4.0]-7-undecene; inorganic bases, such as sodium carbonate, potassium carbonate, sodium hydrogencarbonate, potassium hydrogencarbonate, sodium hydroxide, and sodium hydride; metal amides, such as sodium amide and lithium diisopropylamide; and alcoholates, such as potassium t-butoxide.

The compound of formula (1) used in process 1 is known per se or can be prepared from a ketone compound of formula (14) as follows.

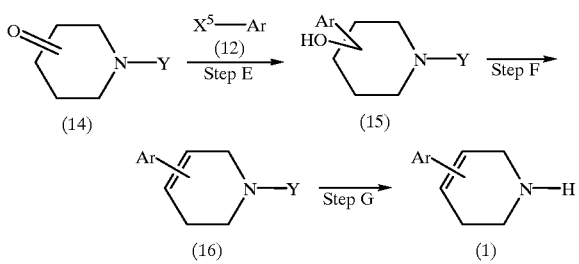

Where the protective group Y of the ketone compound (14) is an alkoxycarbonyl group, an acyl group or a sulfonyl group, the compound (14) is led to a compound of formula (16) under the same conditions as in steps E and F. That is, the compound of formula (14) reacts with a metal compound, which is obtained from the compound of formula (12) and a metal reagent, to give an alcohol compound (15), which is then treated with an acid, such as an inorganic acid, e.g., hydrochloric acid, hydrobromic acid or sulfuric acid, an organic acid, e.g., trifluoroacetic acid, formic acid or methanesulfonic acid, a dioxane or ethyl acetate solution of hydrogen chloride, etc. In this case, dehydration and removal of the protective group are carried out simultaneously or stepwise to obtain the compound of formula (16) in which Y is a hydrogen atom, i.e., the compound of formula (1). In case only a dehydration reaction precedes, removal of the protective group Y can be achieved even with an inorganic base, such as sodium hydroxide, potassium hydroxide or barium hydroxide, to give the compound of formula (16) in which Y is a hydrogen atom. Where the alcohol of formula (15) is converted to its active species in the same manner as in step F followed by dehydration, the protective group is removed by the above-described acid or base treatment.

Step G:

Where the protective group Y of the ketone compound (14) is an alkyl group having 1 to 5 carbon atoms or a benzyl group, the protective group is removed after steps E and F as follows. The protective group is once converted to an alkoxycarbonyl group by reaction with a haloalkyl formate, such as chloroethyl formate, in the presence or absence of an inorganic base, such as sodium carbonate or potassium carbonate, or an organic base, such as triethylamine or N,N-diisopropylethylamine, and the alkoxycarbonyl group is then removed under a basic or acidic condition in the same manner as described above to obtain the compound represented by formula (1).

The compound of the invention is useful as a treating agent or a prophylactic agent for diseases which CRF is said to participate in. For this purpose, the compound of the invention can be formulated into tablets, pills, capsules, granules, powders, solutions, emulsions, suspensions, injections, and so forth together with commonly employed extenders, binders, disintegrants, pH adjustors, solubilizers, and the like in accordance with common preparation techniques.

The compound of the invention can be administered orally or non-orally at a dose of 0.1 to 500 mg/day for an adult in a single dose or several divided doses. The dose is subject to variation appropriately depending on the disease and the age, body weight or symptoms of a patient.

BEST MODES FOR CARRYING OUT THE INVENTION

The present invention will now be illustrated specifically by way of Examples and Test Example.

EXAMPLE 1

Synthesis of 2-[N-(2-bromo-4-isopropylphenyl)-N-ethylamino]-4-(4-phenyl-1,2,3,6-tetrahydropyridin-1-yl)-6-methylpyrimidine hydrochloride:

(1) In 4 ml of ethanol was dissolved 415 mg of 2,4-dichloro-6-methylpyrimidine, and the solution was cooled with ice-water. To the solution were added 503 mg of 4-phenyl-1,2,3,6-tetrahydropyridine hydrochloride and 664 mg of diisopropylethylamine, followed by stirring overnight under cooling with ice. The reaction solution was poured into a saturated aqueous solution of sodium hydrogencarbonate and extracted with ethyl acetate. The extract was washed with a saturated aqueous sodium chloride solution and dried over anhydrous sodium sulfate. The desiccant was removed by filtration, the filtrate was concentrated under reduced pressure, and the residue was purified by silica gel column chromatography (developing solvent: hexane/ethyl acetate=10/1 to 3/1) to give 491 mg of 4-(4-phenyl-1,2,3,6-tetrahydropyridin-1-yl)-2-chloro-6-methylpyrimidine as crystals.

(2) 4-(4-Phenyl-1,2,3,6-tetrahydropyridin-1-yl)-2-chloro-6-methylpyrimidine (466 mg), 408 mg of 2-bromo-4-isopropylaniline hydrochloride and 232 mg of diisopropylethylamine were heated in 5 ml of ethylene glycol under reflux for 1 hour. The reaction solution was poured into a saturated aqueous solution of sodium hydrogencarbonate and extracted with ethyl acetate. The extract was washed successively with water and a saturated aqueous solution of sodium chloride and dried over anhydrous sodium sulfate. The desiccant was filtered off, the solvent was concentrated under reduced pressure, and the residue was purified by silica gel column chromatography (developing solvent: hexane/ethyl acetate=6/1) to give 458 mg of 2-[N-(2-bromo-4-isopropylphenyl)amino]-4-(4-phenyl-1,2,3,6-tetrahydropyridin-1-yl)-6-methylpyrimidine as an amorphous substance.

(3) In 5 ml of N,N-dimethylformamide was dissolved 453 mg of 2-[N-(2-bromo-4-isopropylphenyl)amino]-4-(4-phenyl-1,2,3,6-tetrahydropyridin-1-yl)-6-methylpyrimidine, and 51 mg of a 60% oil dispersion of sodium hydride was added thereto. The mixture was stirred at room temperature for 1 hour. To the mixture was added 214 mg of ethyl iodide, followed by stirring at room temperature overnight. The reaction solution was poured into water and extracted with ethyl acetate. The extract was washed successively with water and a saturated sodium chloride aqueous solution, and dried over anhydrous sodium sulfate. The desiccant was filtered off, the filtrate was concentrated under reduced pressure, and the residue was purified by silica gel column chromatography (developing solvent: hexane/ethyl acetate=8/1). The resulting free amine was converted to its hydrochloride by treatment with 4N HCl/ethyl acetate in methanol, and crystallized from ether to give 325 mg of 2-[N-(2-bromo-4-isopropylphenyl)-N-ethylamino]-4-(4-phenyl-1,2,3,6-tetrahydropyridin-1-yl)-6-methylpyrimidine hydrochloride The structure and physical properties data of the resulting compound and other compounds obtained similarly are shown in Table 1.

EXAMPLE 2

Synthesis of 2-[N-(2,4-dimethoxyphenyl)-N-ethylamino]-4-[4-(3,4-dichlorophenyl-1,2,3,6-tetrahydropyridin-1-yl]-6-methylpyrimidine:

4-[4-(3,4-Dichlorophenyl)-1,2,3,6-tetrahydropyridin-1-yl]-2-chloro-6-methylpyrimidine (500 mg), which was obtained from 2,4-dichloro-6-methylpyrimidine and 4-(3,4-dichlorophenyl)-1,2,3,6-tetrahydropyridine in the same manner as in Example 1, and 281 mg of N-ethyl-2,4-dimethoxyaniline were heated in 2 ml of ethylene glycol at 170° C. for 1.5 hours. The reaction solution was poured into a saturated aqueous solution of sodium hydrogencarbonate and extracted with ethyl acetate. The extract was washed successively with water and a saturated sodium chloride aqueous solution, and dried over anhydrous sodium sulfate. The desiccant was removed by filtration, the filtrate was concentrated under reduced pressure, and the residue was purified by silica gel column chromatography (developing solvent: hexane/ethyl acetate=4/1) and recrystallized from diethyl ether to give 360 mg of 2-[N-(2,4-dimethoxyphenyl)-N-ethylamino]-4-[4-(3,4-dichlorophenyl)-1,2,3,6-tetrahydropyridin-1-yl]-6-methylpyrimidine.

The structure and physical properties data of the resulting compound and other compounds obtained similarly are shown in Table 1.

EXAMPLE 3

Synthesis of 2-[N-(2-bromo-4-isopropylphenyl)-N-ethylamino]-4-[4-(3-chlorophenyl)-1,2,3,6-tetrahydropyridin-1-yl]-6-methylpyrimidine hydrochloride:

(1) 2-[N-(2-Bromo-4-isopropylphenyl)-N-ethylamino]-4-[4-(1,3-dioxolan-2-yl)piperidin-1-yl]-6-methylpyrimidine (14.25 g), which was obtained from 2,4-dichloro-6-methylpyrimidine and 4-(1,3-dioxolan-2-yl)piperidine in the same manner as in Example 1, was dissolved in 75 ml of tetrahydrofuran, and 75 ml of 4N hydrochloric acid was added thereto, followed by stirring at room temperature for 6 hours. The reaction solution was concentrated under reduced pressure to about 80 ml. The concentrate was poured into a saturated aqueous solution of sodium hydrogencarbonate and extracted with ethyl acetate. The extract was washed with a saturated aqueous solution of sodium chloride and dried over anhydrous sodium sulfate. The desiccant was removed by filtration, the filtrate was concentrated under reduced pressure, and the residue was purified by silica gel column chromatography (developing solvent: hexane/ethyl acetate=7/1 to 6/1) to give 12.93 g of 2-[N-(2-bromo-4-isopropylphenyl)-N-ethylamino]-6-methyl-4-(4-oxopiperidin-1-yl)pyrimidine as an oily substance.

(2) 3-Bromochlorobenzene (427 mg), 27 mg of magnesium, and a trace amount of iodine were heated in 5 ml of tetrahydrofuran under reflux for 1 hour. The reaction mixture was cooled with ice and added dropwise to a solution of 321 mg of 2-[N-(2-bromo-4-isopropylphenyl)-N-ethylamino]-6-methyl-4-(4-oxopiperidin-1-yl)pyrimidine in 3 ml of tetrahydrofuran, followed by stirring under ice-cooling for 1 hour and then at room temperature for an addition 1 hour period. The reaction mixture was again cooled with ice, and a saturated ammonium chloride aqueous solution was added thereto dropwise. After stirring at room temperature for 10 minutes, the mixture was extracted with ethyl acetate. The extract was washed successively with a saturated ammonium chloride aqueous solution, a saturated sodium hydrogencarbonate aqueous solution and a saturated sodium chloride aqueous solution, and dried over anhydrous sodium sulfate. The desiccant was removed by filtration, the filtrate was concentrated under reduced pressure, and the residue was purified by silica gel column chromatography (developing solvent: hexane/ethyl acetate=4/1) to give 238 mg of 2-[N-(2-bromo-4-isopropylphenyl)-N-ethylamino]-4-[4-(3-chlorophenyl)-4-hydroxypiperidin-1-yl]-6-methylpyrimidine.

(3) To 170 mg of 2-[N-(2-bromo-4-isopropylphenyl)-N-ethylamino]-4-[4-(3-chlorophenyl)-4-hydroxypiperidin-1-yl]-6-methylpyrimidine was added 1.25 ml of trifluoroacetic acid, followed by stirring at room temperature for 2 days. The reaction solution was concentrated under reduced pressure, and a saturated aqueous solution of sodium hydrogencarbonate was added to the residue. The mixture was extracted with ethyl acetate, and the extract was washed successively with a saturated sodium hydrogencarbonate aqueous solution and a saturated sodium chloride aqueous solution, and dried over anhydrous sodium sulfate. The desiccant was filtered off, the filtrate was concentrated under reduced pressure, and the residue was purified by silica gel column chromatography (developing solvent: hexane/ethyl acetate=7/1). The resulting free amine was converted to its hydrochloride by treating with 4N HCl/ethyl acetate in methanol, and recrystallized from isopropyl alcohol-diisopropyl ether to give 131 mg of 2-[N-(2-bromo-4-isopropylphenyl)-N-ethylaminol-4-[4-(3-chlorophenyl)-1,2,3,6-tetrahydropyridin-1-yl]-6-methylpyrimidine hydrochloride.

The structure and physical properties data of the resulting compound and other compounds obtained similarly are shown in Table 1.

EXAMPLE 4

Synthesis of 2-[N-(2-bromo-4-isopropylphenyl)-N-ethylamino]-4-[4-(furan-2-yl)-1,2,3,6-tetrahydropyridin-1-yl]-6-methylpyrimidine:

(1) To a solution of 136 mg of furan in 1 ml of tetrahydrofuran was added dropwise 0.9 ml of a 1.63M n-hexane solution of n-butyl lithium under cooling at −15° C. over 10 minutes, followed by stirring at 5° C. for 20 minutes. To the reaction mixture was added dropwise a solution of 432 mg of 2-[N-(2-bromo-4-isopropylphenyl)-N-ethylamino]-6-methyl-4-(4-oxopiperidin-1-yl)pyrimidine in 2 ml of tetrahydrofuran over 10 minutes while cooling to −15° C., followed by stirring at −15° to 0° C. for 30 minutes. After stirring at room temperature for 1 hour, a saturated aqueous solution of ammonium chloride was added thereto dropwise under ice-cooling, and the mixture was extracted with ethyl acetate. The extract was washed successively with a saturated ammonium chloride aqueous solution, a saturated sodium hydrogencarbonate aqueous solution and a saturated sodium chloride aqueous solution, and dried over anhydrous sodium sulfate. The desiccant was removed by filtration, the filtrate was concentrated under reduced pressure, and the residue was purified by silica gel column chromatography (developing solvent: hexane/ethyl acetate=3/1) to give 279 mg of 2-[N-(2-bromo-4-isopropylphenyl)-N-ethylamino]-4-[4-(furan-2-yl)-4-hydroxypiperidin-1-yl]-6-methylpyrimidine.

(2) A solution of 48 mg of methanesulfonyl chloride in 0.5 ml of dichloromethane was added dropwise under ice-cooling to a solution of 104 mg of 2-[N-(2-bromo-4-isopropylphenyl)-N-ethylamino]-4-[4-(furan-2-yl)-4-hydroxypiperidin-1-yl]-6-methylpyrimidine, 85 mg of triethylamine, and 13 mg of 4-dimethylaminopyridine in 1 ml of dichloromethane, followed by stirring for 15 minutes and then at room temperature for 2 hours. The reaction solution was poured into a saturated sodium hydrogencarbonate aqueous solution and extracted with ethyl acetate. The extract was washed successively with a saturated sodium hydrogencarbonate aqueous solution and a saturated sodium chloride aqueous solution, and dried over anhydrous sodium sulfate. The desiccant was filtered off, the filtrate was concentrated under reduced pressure, and the residue was purified by silica gel column chromatography (developing solvent: hexane/ethyl acetate=9/1) to give 70 mg of 2-[N-(2-bromo-4-isopropylphenyl)-N-ethylamino]-4-[4-(furan-2-yl)-1,2,3,6-tetrahydropyridin-1-yl]-6-methylpyrimidine.

The structure and physical properties data of the resulting compound and other compounds obtained similarly are shown in Table 1.

EXAMPLE 5

Synthesis of 2-[N-(2-bromo-4-isopropylphenyl)-N-ethylamino]-4-[4-(thiophen-2-yl)-1,2,3,6-tetrahydropyridin-1-yl]-6-methylpyrimidine:

(1) The operation of Example 4-(1) was followed using 168 mg of thiophene and 432 mg of 2-[N-(2-bromo-4-isopropylphenyl)-N-ethylamino]-6-methyl-4-(4-oxopiperidin-1-yl)pyrimidine to give 228 mg of 2-(N-(2-bromo-4-isopropylphenyl)-N-ethylamino]-4-[4-(thiophen-2-yl)-4-hydroxypiperidin-l-yl]-6-methylpyrimidine.

(2) 2-[N-(2-Bromo-4-isopropylphenyl)-N-ethylamino]-4-[4-(thiophen-2-yl)-4-hydroxypiperidin-1-yl]-6-methylpyrimidine (166 mg) was stirred in 0.5 ml of 99% formic acid at room temperature for 2 hours. The reaction solution was poured into a saturated aqueous solution of sodium hydrogencarbonate and extracted with ethyl acetate. The extract was washed successively with a saturated sodium hydrogencarbonate aqueous solution and a saturated sodium chloride aqueous solution, and dried over anhydrous sodium sulfate. The desiccant was filtered off, the filtrate was concentrated under reduced pressure, and the residue was purified by silica gel column chromatography (developing solvent: hexane/ethyl acetate=5/1) to give 132 mg of 2-[N-(2-bromo-4-isopropylphenyl)-N-ethylamino]-4-[4-(thiophen-2-yl)-1,2,3,6-tetrahydropyridin-1-yl]-6-methylpyrimidine.

The structure and physical properties data of the resulting compound and other compounds obtained similarly are shown in Table 1.

TABLE 1

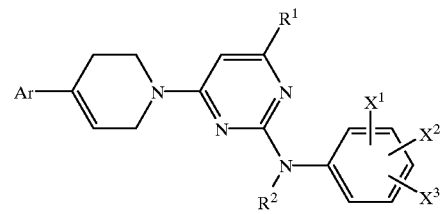

| Comp. No.*1 | Exp. No.*2 | Ar | $X^1$ | $X^2$ | $X^3$ | $R^1$ | $R^2$ | Salt | m.p. (Recry. Sol.*3) (° C.) |
|---|---|---|---|---|---|---|---|---|---|
| 1-01 | 1 | Ph | 2-Br | 4-i-Pr | H | Me | Et | HCl | 123.5–126.5 ($Et_2O$*4) |
| 1-02 | 1 | 3-F-Ph | 2-Br | 4-i-Pr | H | Me | Et | HCl | 117.5–120.0 (AcOEt*4) |
| 1-03 | 1 | 3-F-Ph | 2-Br | 4-i-Pr | H | Me | CH=C—$CH_2$ | HCl | 118.5–123.5 (AcOEt/IPE*4) |
| 1-04 | 1 | 3-F-Ph | 2-Br | 4-t-Bu | H | Me | Et | HCl | 137.0–142.0 (IPA/IPE) |
| 1-05 | 1 | 3-F-Ph | 2-I | 4-i-Pr | H | Me | Et | $H_2SO_4$ | 248.0–249.0 (EtOH) |
| 1-06 | 1 | 3-F-Ph | 2-MeS | 4-i-Pr | H | Me | Et | HCl | 125.0–128.0 (IPA/IPE) |
| 1-07 | 2 | 3-F-Ph | 2-MeS | 4-i-Pr | H | Me | c-Pr$CH_2$ | HCl | 164.0–174.0 (AcOEt) |
| 1-08 | 1 | 3-F-Ph | 2-MeS | 4-i-Pr | H | Me | CH=C—$CH_2$ | HCl | 92.0–95.0 (AcOEt/$Et_2O$*4) |
| 1-09 | 1 | 3-F-Ph | 2-MeS | 4-t-Bu | H | Me | Et | HCl | 144.0–148.0 (AcOEt) |
| 1-10 | 1 | 3-F-Ph | 2-EtS | 4-i-Pr | H | Me | Et | HCl | 138.0–140.5 (AcOEt/$Et_2O$*4) |
| 1-11 | 1 | 3-F-Ph | 2-i-PrS | 4-i-Pr | H | Me | Et | HCl | 112.0–117.0 (AcOEt/$Et_2O$*4) |

TABLE 1-continued

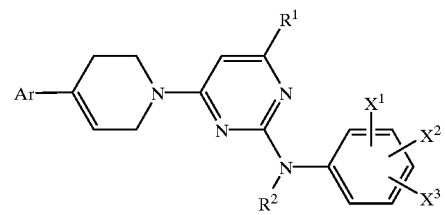

| Comp. No.*1 | Exp. No.*2 | Ar | X¹ | X² | X³ | R¹ | R² | Salt | m.p. (Recry. Sol.*3) (° C.) |
|---|---|---|---|---|---|---|---|---|---|
| 1-12 | 1 | 3-F-Ph | 2-Br | 4-Me₂N | H | Me | Et | HCl | 116.0–119.0 (AcOEt*4) |
| 1-13 | 2 | 3-F-Ph | 2-MeO | 4-MeO | H | Me | Et | — | 127.0–129.0 (Et₂O) |
| 1-14 | 2 | 3-F-Ph | 2-Me | 4-Me | 6-Me | Me | Et | HCl | 126.5–129.0 (AcOEt/IPE*4) |
| 1-15 | 3 | 4-F-Ph | 2-Br | 4-i-Pr | H | Me | Et | HCl | 183.0–185.0 (IPA/IPE) |
| 1-16 | 1 | 4-F-Ph | 2-MeS | 4-i-Pr | H | Me | Et | HCl | 136.0–139.0 (IPA/IPE) |
| 1-17 | 1 | 4-F-Ph | 2-Br | 4-Me₂N | H | Me | Et | HCl | 121.5–124.0 (IPA/IPE) |
| 1-18 | 2 | 4-F-Ph | 2-MeO | 4-MeO | H | Me | Et | — | 181.5–182.5 (AcOEt) |
| I-19 | 2 | 4-F-Ph | 2-Me | 4-Me | 6-Me | Me | Et | HCl | 131.0–134.0 (IPA/IPE) |
| I-20 | 3 | 3,4-F2-Ph | 2-Br | 4-i-Pr | H | Me | Et | HCl | 173.0–174.0 (IPA/IPE) |
| I-21 | 1 | 3,4-F2-Ph | 2-MeS | 4-i-Pr | H | Me | Et | HCl | 128.5–131.5 (IPA/IPE) |
| I-22 | 1 | 3,4-F2-Ph | 2-Br | 4-Me₂N | H | Me | Et | HCl | 108.0–111.0 (IPA/IPE) |
| I-23 | 2 | 3,4-F2-Ph | 2-MeO | 4-MeO | H | Me | Et | — | 162.0–162.5 (AcOEt) |
| I-24 | 2 | 3,4-F2-Ph | 2-Me | 4-Me | 6-Me | Me | Et | HCl | 128.0–130.5 (IPA/IPE) |
| I-25 | 1 | 3,5-F2-Ph | 2-Br | 4-i-Pr | H | Me | Et | HCl | 126.0–131.0 (EtOH/IPE) |
| I-26 | 1 | 3,5-F2-Ph | 2-MeS | 4-i-Pr | H | Me | Et | HCl | 127.5–132.0 (AcOEt*4) |
| I-27 | 1 | 3,5-F2-Ph | 2-MeS | 4-i-Pr | H | Me | CH=C—CH₂ | HCl | 115.0–120.0 (AcOEt/Et₂O*4) |
| I-28 | 1 | 3-Cl-Ph | 2-Br | 4-Me | H | Me | Et | HCl | 140.0–140.5 (IPA/IPE) |
| I-29 | 1 | 3-Cl-Ph | 2-Br | 4-n-Pr | H | Me | Et | HCl | 156.0–156.5 (IPA/IPE) |
| I-30 | 3 | 3-Cl-Ph | 2-Br | 4-i-Pr | H | Me | Et | HCl | 173.5–175.0 (IPA/IPE) |
| I-31 | 1 | 3-Cl-Ph | 2-Br | 4-i-Pr | H | Me | CH=C—CH₂ | HCl | 113.0–118.0 (AcOEt/IPE*4) |
| I-32 | 1 | 3-Cl-Ph | 2-Br | 4-t-Bu | H | Me | Et | HCl | 145.0–150.0 (IPA/IPE) |
| I-33 | 1 | 3-Cl-Ph | 2-Br | 4-Me₂N | H | Me | Et | — | amorphous *5 |
| I-34 | 1 | 3-Cl-Ph | 2-MeS | 4-i-Pr | H | Me | Et | HCl | 124.5–127.5 (IPA/IPE) |
| I-35 | 2 | 3-Cl-Ph | 2-MeS | 4-i-Pr | H | Me | c-PrCH₂ | HCl | 163.5–173.5 (AcOEt) |
| I-36 | 1 | 3-Cl-Ph | 2-MeS | 4-i-Pr | H | Me | CH=C—CH₂ | HCl | 105.0–110.0 (AcOEt/IPE*4) |
| I-37 | 1 | 3-Cl-Ph | 2-Me | 4-Et₂N | H | Me | Et | 2HCl | amorphous*5 |
| I-38 | 2 | 3-Cl-Ph | 2-MeO | 4-MeO | H | Me | Et | — | 133.0–134.5 (Et₂O) |
| I-39 | 2 | 3-Cl-Ph | 2-Me | 4-Me | 6-Me | Me | Et | HCl | 120.0–122.5 (IPA/IPE) |
| I-40 | 1 | 4-Cl-Ph | 2-Br | 4-i-Pr | H | Me | Me | HCl | 106.0–109.0 (AcOEt*4) |
| I-41 | 1 | 4-Cl-Ph | 2-Br | 4-i-Pr | H | Me | Et | — | 91.0–92.0 (Hex) |
| I-42 | 1 | 4-Cl-Ph | 2-Br | 4-i-Pr | H | Me | n-Pr | HCl | 137.0–1140.0 (AcOEt*4) |
| I-43 | 1 | 4-Cl-Ph | 2-Br | 4-i-Pr | H | Me | n-Pen | HCl | 118.0–120.5 (AcOEt*4) |
| I-44 | 1 | 4-Cl-Ph | 2-Br | 4-i-Pr | H | Me | i-Bu | HCl | 124.0–127.0 (AcOEt*4) |
| I-45 | 1 | 4-Cl-Ph | 2-Br | 4-i-Pr | H | Me | CH₂=CH—CH₂ | HCl | 109.0–112.0 (AcOEt*4) |
| I-46 | 1 | 4-Cl-Ph | 2-Br | 4-i-Pr | H | Me | CH=C—CH₂ | HCl | 120.5–123.0 (AcOEt*4) |
| I-47 | 1 | 4-Cl-Ph | 2-Br | 4-i-Pr | H | H | Et | — | amorphous*7 |
| I-48 | 1 | 4-Cl-Ph | 2-Br | 4-c-Pen | H | Me | Et | HCl | 133.0–138.0 (EtOH/IPE) |
| I-49 | 1 | 4-Cl-Ph | 2-Br | 4-i-Pr | H | i-Pr | Et | — | amorphous*5 |
| I-50 | 1 | 4-Cl-Ph | 2-MeS | 4-n-Pr | H | Me | Et | HCl | 125.0–128.5 (AcOEt*4) |
| I-51 | 1 | 4-Cl-Ph | 2-MeS | 4-i-Pr | H | Me | Et | HCl | 134.5–135.0 (AcOEt*4) |
| I-52 | 1 | 4-Cl-Ph | 2-MeS | 4-i-Pr | H | Me | CH=C—CH₂ | HCl | 111.0–115.5 (AcOEt/Et₂O*4) |
| I-53 | 1 | 4-Cl-Ph | 2-MeS | 4-n-Bu | H | Me | Et | HCl | 120.0–123.0 (AcOEt*4) |
| I-54 | 2 | 4-Cl-Ph | 2-MeS | 4-c-Pen | H | Me | Et | HCl | 131.5–136.5 (EtOH/IPE) |
| I-55 | 1 | 4-Cl-Ph | 2-Br | 4-Me₂O | H | Me | Et | HCl | 115.5–118.5 (IPA/IPE) |
| I-56 | 1 | 4-Cl-Ph | 2-Cl | 4-Cl | H | Me | Et | HCl | 112.0–114.0 (IPA/IPE) |
| I-57 | 1 | 4-Cl-Ph | 2-Br | 4-Br | H | Me | Et | HCl | 111.0–114.0 (IPA/IPE) |
| I-58 | 2 | 4-Cl-Ph | 2-MeO | 4-MeO | H | Me | Et | — | 159.0–159.5 (Et₂O) |
| I-59 | 2 | 4-Cl-Ph | 2-Me | 4-Me | 6-Me | Me | Et | HCl | 125.0–127.0 (IPA/IPE) |
| I-60 | 1 | 4-Br-Ph | 2-Br | 4-i-Pr | H | Me | Et | HCl | 118.5–121.5 (IPA) |
| I-61 | 1 | 3,4-Cl₂-Ph | 2-Br | 4-i-Pr | H | Me | Et | HCl | 126.5–129.5 (IPA/IPE) |
| I-62 | 1 | 3,4-Cl₂-Ph | 2-MeS | 4-i-Pr | H | Me | Et | HCl | 116.5–119.0 (IPA/IPE) |
| I-63 | 1 | 3,4-Cl₂-Ph | 2-MeS | 4-i-Pr | H | Me | CH=C—CH₂ | HCl | 122.5–127.5 (AcOEt/Et₂O*4) |
| I-64 | 2 | 3,4-Cl₂-Ph | 2-MeO | 4-MeO | H | Me | Et | — | 154.0–155.5 (Et₂O) |
| I-65 | 2 | 3,4-Cl₂-Ph | 2-Me | 4-Me | 6-Me | Me | Et | HCl | 115.0–118.0 (AcOEt/Et₂O*4) |
| I-66 | 1 | 3-CF₂-Ph | 2-Br | 4-i-Pr | H | Me | Et | HCl | 127.0–130.0 (IPA/IPE) |
| I-67 | 1 | 3-CF₂-Ph | 2-Br | 4-Me₂O | H | Me | Et | HCl | 106.5–109.5 (IPA/IPE) |
| I-68 | 1 | 3-CF₂-Ph | 2-MeS | 4-i-Pr | H | Me | Et | HCl | 115.0–117.5 (IPA/IPE) |
| I-69 | 1 | 3-CF₂-Ph | 2-MeS | 4-i-Pr | H | Me | CH=C—CH₂ | HCl | 106.5–111.5 (AcOEt/Et₂O*4) |
| I-70 | 2 | 3-CF₂-Ph | 2-MeO | 4-MeO | H | Me | Et | HCl | 108.0–110.0 (IPA/IPE) |
| I-71 | 2 | 3-CF₂-Ph | 2-Me | 4-Me | 6-Me | Me | Et | HCl | 107.5–110.0 (Et₂O*4) |
| I-72 | 3 | 2-Me-Ph | 2-Br | 4-i-Pr | H | Me | Et | HCl | 176.5–179.0 (IPA/IPE) |
| I-73 | 3 | 3-Me-Ph | 2-Br | 4-i-Pr | H | Me | Et | HCl | 162.0–165.0 (IPA/IPE) |
| I-74 | 3 | 4-Me-Ph | 2-Br | 4-i-Pr | H | Me | Et | HCl | 161.0–164.0 (IPA/IPE) |
| I-75 | 3 | 2-MeO-Ph | 2-Br | 4-i-Pr | H | Me | Et | HCl | 160.0–160.5 (IPA/IPE) |

TABLE 1-continued

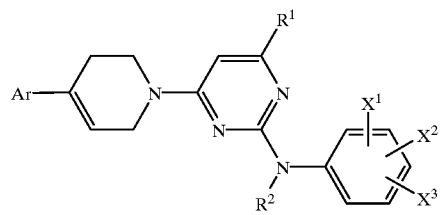

| Comp. No.*[1] | Exp. No.*[2] | Ar | $X^1$ | $X^2$ | $X^3$ | $R^1$ | $R^2$ | Salt | m.p. (Recry. Sol.*[3]) (° C.) |
|---|---|---|---|---|---|---|---|---|---|
| I-76 | 3 | 3-MeO-Ph | 2-Br | 4-i-Pr | H | Me | Et | HCl | 149.0–152.0 (IPA/IPE) |
| I-77 | 3 | 4-MeO-Ph | 2-Br | 4-i-Pr | H | Me | Et | HCl | 134.5–135.0 (IPA/IPE) |
| I-78 | 5 | 2-Thi*[9] | 2-Br | 4-i-Pr | H | Me | Et | — | amorphous*[10] |
| I-79 | 4 | 2-Fur*[11] | 2-Br | 4-i-Pr | H | Me | Et | — | amorphous*[12] |

Note:
*[1]: Compound No.
*[2]: Example No. used for synthesis
*[3]: Recrystallizing solvent;
Et$_2$O: diethyl ether
IPA: isopropyl alcohol
IPE: diisopropyl ether
AcOEt: ethyl acetate
Hex: hexane
*[4]: Crystallizing solvent
*[5]: NMR (CDCl$_3$) δ (ppm): 1.20 (t, J=7.1Hz), 2.22 (3H, s), 2.40–2.61 (2H, m), 2.98 (6H, s), 3.52–4.28 (6H, m), 5.79 (1H, s), 6.10 (1H, s), 6.68 (1H, dd, j=8.8, 2.9Hz), 6.99 (1H, d, j=2.9Hz), 7.10 (1H, d, j=8.8Hz), 7.19–7.42 (4H, m) EIMS m/e: 525 (M$^+$), 446 (100%)
*[6]: NMR (CDCl$_3$) δ (ppm): 1.00–1.67 (9H, m), 1.80–3.00 (8H, m), 3.00–4.40 (10H, m), 5.75–8.10 (9H, m) EIMS m/e: 489 (M$^+$, 100%)
*[7]: NMR (CDCl$_3$) δ (ppm): 1.18–1.33 (3H, m), 1.27 (6H, d, J=6.8Hz), 2.45–2.63 (2H, m), 2.91 (1H, sept, J=7.0Hz), 3.5 (0–4.30 (6H, m), 5.92 (1H, d, J=6.0Hz), 6.04–6.16 (1H, m), 7.14–7.26 (2H, m), 7.31 (4H, s), 7.50–7.56 (1H, m), 7.96 (1H, d, J=6.0Hz) FABMS m/e: 511 (MH$^+$, 100%)
*[8]: NMR (CDCl$_3$) δ (ppm): 1.17 (6H, br d, J=6.6Hz), 1.24 (3H, t, J=7.0), 1.28 (6H, d, J=7.0Hz), 2.40–2.75 (3H, m), 2.92 (1H, sept, J=7.0Hz), 3.50–4.28 (6H, m), 5.79 (1H, s), 6.00–6.11 (1H, m), 7.11–7.24 (2H, m), 7.30 (4H, s), 7.50 (1H, s) EIMS m/e: 552 (M$^+$), 473 (100%)
*[9]: 2-Thienyl
*[10]: NMR (CDCl$_3$) δ (ppm): 1.21 (3H; t, J=7.1Hz), 1.28 (6H, d, J=7.0Hz), 2.21 (3H, s), 2.43–2.60 (2H, m), 2.93 (1H, sept, J=7.0Hz), 3.60–4.30 (6H, m), 5.80 (1H, s), 6.03–6.15 (1H, m), 6.92–7.00 (2H, m), 7.10–7.20 (3H, m), 7.51 (1H, s) CIMS m/e: 497 (MH$^+$, 100%)
*[11]: 2-Furyl
*[12]: NMR (CDCl$_3$) δ (ppm): 1.21 (3H, t, J=7.1Hz), 1.28 (6H, d, J=6.9Hz), 2.21 (3H, s), 2.31–2.47 (2H, m), 2.92 (1H, sept, J=6.9Hz), 3.55–4.30 (6H, m), 15.79 (1H, s), 6.13–6.25 (2H, m), 6.37 (1H, dd, J=3.31 1.8Hz), 7.13–7.20 (2H, m), 7.34 (1H, d, J=1.8Hz), 7.51 (1H, s) FABMS m/e: 481 (MH$^+$, 100%)

EXAMPLE 6

Synthesis of 2-[N-(2-bromo-4-isopropylphenyl)-N-ethylamino]-4-(5-phenyl-1,2,3,6-tetrahydropyridin-1-yl)-6-methylpyrimidine hydrochloride:

(1) A solution of 5.00 g of N-t-butoxycarbonyl-3-oxopiperidine in 10 ml of tetrahydrofuran was added dropwise under ice-cooling to a Grignard reagent solution prepared from 4.73 g of bromobenzene and 0.79 g of magnesium in 50 ml of tetrahydrofuran. The mixture was stirred at room temperature for 1 hour, followed by cooling with ice, and 100 ml of a saturated aqueous solution of ammonium chloride was added thereto dropwise. The reaction mixture was extracted with ethyl acetate, and the extract was washed successively with a saturated aqueous solution of sodium hydrogencarbonate and a saturated aqueous solution of sodium chloride, and dried over anhydrous sodium sulfate. The desiccant was filtered off, the filtrate was concentrated under reduced pressure, and the residue was purified by silica gel column chromatography (developing solvent: hexane/ethyl acetate=3/1) to give 4.21 g of N-t-butoxycarbonyl-3-hydroxy-3-phenylpiperidine.

(2) To 3.63 g of N-t-butoxycarbonyl-3-hydroxy-3-phenylpiperidine was added 49.2 ml of trifluoroacetic acid, and the mixture was stirred at room temperature overnight and then heated under reflux for 5 hours. The reaction mixture was concentrated under reduced pressure, and the residue was dissolved in 10 ml of dichloromethane. To the solution was added 6 ml of 4N hydrogen chloride in dioxane, followed by concentration under reduced pressure.

The resulting residue was dissolved in 35 ml of ethanol, 5.16 g of diisopropylethylamine and 2.60 mg of 2,4-dichloro-6-methylpyrimidine were added thereto, and the mixture was stirred overnight under cooling with ice. The reaction solution was poured into a saturated aqueous solution of sodium hydrogencarbonate and extracted with ethyl acetate. The extract was washed with a saturated sodium chloride aqueous solution and dried over anhydrous sodium sulfate. The desiccant was removed by filtration, the filtrate was concentrated under reduced pressure, and the residue was purified by silica gel column chromatography (developing solvent: hexane/ethyl acetate=3/1) to give 2.17 mg of 4-(5-phenyl-1 2,3, 6-tetrahydropyridin-1-yl) -2-chloro-6-methylpyrimidine as crystals.

(3) 4-(5-Phenyl-1,2,3,6-tetrahydropyridin-1-yl)-2-chloro-6-methylpyrimidine (1.10 g), 2-bromo-4-isopropylaniline hydrochloride (0.97 g), and diisopropylethylamine (0.50 g) were heated at reflux in 5 ml of ethylene glycol for 1 hour. The reaction solution was poured into a saturated sodium hydrogencarbonate aqueous solution and extracted with ethyl acetate. The extract was washed with water and then with a saturated sodium chloride aqueous solution, and dried over anhydrous sodium sulfate. The desiccant was filtered off, and the filtrate was concentrated under reduced pressure. The residue was purified by silica gel column chromatography (developing solvent: hexane/ethyl acetate=3/1) to give 1.32 g of 2-[N-(2-bromo-4-isopropylphenyl)amino]-4-(5-phenyl-1,2,3,6-tetrahydropyridin-1-yl)-6-methylpyrimidine as an amorphous substance.

(4) In 12 ml of N,N-dimethylformamide was dissolved 1.21 g of 2-[N-(2-bromo-4-isopropylphenyl)amino]-4-(5-phenyl-1,2,3,6-tetrahydropyridin-1-yl)-6-methylpyrimidine, and 136 mg of a 60% oil dispersion of sodium hydride was added to the solution, followed by stirring at room temperature for 1 hour. To the mixture was added 570 mg of ethyl iodide, and the mixture was stirred at room temperature overnight. The reaction solution was poured into water and extracted with ethyl acetate. The extract was washed with water and a saturated sodium chloride aqueous solution, and dried over anhydrous sodium sulfate. The desiccant was removed by filtration, the filtrate was concentrated under reduced pressure, and the residue was purified by silica gel column chromatography (developing solvent: hexane/acetone=9/1). The resulting free amine was converted to its hydrochloride by treatment with 4N HCl/ethyl acetate in methanol, and crystallized from ether to give 1.02 g of 2-[N-(2-bromo-4-isopropylphenyl)-N-ethylamino]-4-(5-phenyl-1,2,3,6-tetrahydropyridin-1-yl)-6-methylpyrimidine hydrochloride.

The structure and physical properties data of the resulting compound and other compounds obtained similarly are shown in Table 2.

EXAMPLE 7

Synthesis of 2-[N-(4-isopropyl-2-methylthiophenyl)-N-ethylamino]-4-[5-(2-methylphenyl)-1,2,3,6-tetrahydropyridin-1-yl]-6-methylpyrimidine hydrochloride:

4-[5-(2-Methylphenyl)-1,2,3,6-tetrahydropyridin-1-yl]-2-chloro-6-methylpyrimidine (905 mg), which was obtained from N-t-butoxycarbonyl-3-oxopiperidine, 2-methylphenylmagnesium bromide, and 2,4-dichloro-6-methylpyrimidine in the same manner as in Example 6, and 632 mg of N-ethyl-4-isopropyl-2-methylthioaniline were heated in 10 ml of ethylene glycol at 170° C. for 1.5 hours. The reaction solution was poured into a saturated sodium hydrogencarbonate aqueous solution and extracted with chloroform. The extract was washed with a saturated sodium chloride aqueous solution and dried over anhydrous sodium sulfate. The desiccant was filtered off, the filtrate was concentrated under reduced pressure, and the residue was purified by silica gel column chromatography (developing solvent: hexane/ethyl acetate=10/1 to 4/1). The resulting free amine was converted to its hydrochloride by treatment with 4N HCl/ethyl acetate in dichloromethane and recrystallized from ethyl acetate/diethyl ether to give 1.05 g of 2-[N-(4-isopropyl-2-methylthiophenyl)-N-ethylamino]-4-[5-(2-methylphenyl)-1,2,3,6-tetrahydropyridin-1-yl]-6-methylpyrimidine hydrochloride.

The structure and physical properties data of the resulting compound and other compounds obtained similarly are shown in Table 2.

TABLE 2

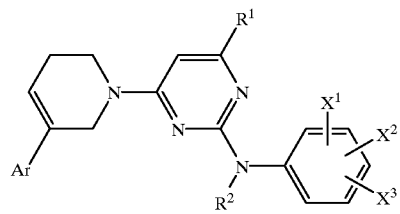

| Comp. No.*[1] | Exp. No.*[2] | Ar | X[1] | X[2] | X[3] | R[1] | R[2] | Salt | m.p. (Recry. Sol.*[3]) (° C.) |
|---|---|---|---|---|---|---|---|---|---|
| 2-01 | 6 | Ph | 2-Br | 4-i-Pr | H | Me | Et | HCl | 137.5–143.5 (IPA/IPE) |
| 2-02 | 6 | 3-F-Ph | 2-Br | 4-i-Pr | H | Me | Et | HCl | 167.0–171.0 (IPA/IPE) |
| 2-03 | 6 | 3-F-Ph | 2-MeS | 4-i-Pr | H | Me | Et | HCl | 140.0–142.0 (AcOEt/Et$_2$O) |
| 2-04 | 6 | 4-F-Ph | 2-Br | 4-i-Pr | H | Me | Et | HCl | 121.5–122.5 (IPA/IPE) |
| 2-05 | 6 | 4-F-Ph | 2-MeS | 4-i-Pr | H | Me | Et | HCl | 144.0–146.5 (AcOEt/Et$_2$O) |
| 2-06 | 6 | 4-F-Ph | 2-Br | 4-Me$_2$N | H | Me | Et | HCl | 115.0–120.0 (IPA/Hex*[4]) |
| 2-07 | 6 | 4-F-Ph | 2-MeS | 4-i-Pr | H | Me | CH=C—CH$_2$ | — | 100.5–102.0 (IPE) |
| 2-08 | 6 | 3-Cl-Ph | 2-Br | 4-i-Pr | H | Me | Et | HCl | 165.0–169.5 (IPA/IPE) |
| 2-09 | 6 | 3-Cl-Ph | 2-MeS | 4-i-Pr | H | Me | Et | HCl | 140.5–146.5 (AcOEt/Et$_2$O) |
| 2-10 | 6 | 4-Cl-Ph | 2-Br | 4-i-Pr | H | Me | Et | — | amorphous*[5] |
| 2-11 | 6 | 4-Cl-Ph | 2-MeS | 4-i-Pr | H | Me | Et | HCl | 135.5–140.0 (AcOEt/Et$_2$O*[4]) |
| 2-12 | 7 | 3,4-F$_2$-Ph | 2-MeS | 4-i-Pr | H | Me | Et | HCl | 127.5–130.0 (IPA/IPE) |
| 2-13 | 7 | 3,5-F$_2$-Ph | 2-MeS | 4-i-Pr | H | Me | Et | HCl | 131.5–135.0 (AcOEt/Et$_2$O*[4]) |
| 2-14 | 7 | 3,4-Cl$_2$-Ph | 2-MeS | 4-i-Pr | H | Me | Et | HCl | 106.0–109.0 (AcOEt*[4]) |
| 2-15 | 7 | 2-Me-Ph | 2-MeS | 4-i-Pr | H | Me | Et | HCl | 128.5–131.5 (AcOEt/Et$_2$O*[4]) |
| 2-16 | 7 | 2-Et-Ph | 2-MeS | 4-i-Pr | H | Me | Et | HCl | 142.0–146.0 (AcOEt/EtOH) |
| 2-17 | 7 | 2-i-Pr-Ph | 2-MeS | 4-i-Pr | H | Me | Et | HCl | 136.0–140.0 (AcOEt/EtOH) |
| 2-18 | 7 | 3-Me-Ph | 2-MeS | 4-i-Pr. | H | Me | Et | HCl | 116.5–119.0 (AcOEt/Et$_2$O*[4]) |
| 2-19 | 7 | 4-Me-Ph | 2-MeS | 4-i-Pr | H | Me | Et | HCl | 147.5–151.5 (IPA/AcOEt*[4]) |
| 2-20 | 7 | 4-MeO-Ph | 2-MeS | 4-i-Pr | H | Me | Et | HCl | 110.5–115.0 (IPA/IPE*[4]) |

Note:
*[1]: Compound No.
*[2]: Example No. used for synthesis
*[3]: Recrystallizing solvent;

TABLE 2-continued

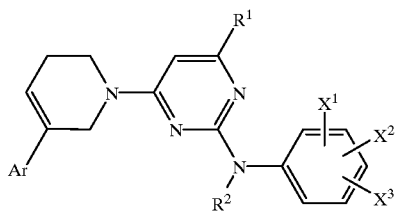

| Comp. No.*[1] | Exp. No.*[2] | Ar | $X^1$ | $X^2$ | $X^3$ | $R^1$ | $R^2$ | Salt | m.p. (Recry. Sol.*[3]) (° C.) |
|---|---|---|---|---|---|---|---|---|---|

IPA: isopropyl alcohol
IPE: diisopropyl ether
AcOEt: ethyl acetate
Hex: hexane
*[4]: Crystallizing solvent
*[5]NMR (CDCl$_3$) δ (ppm): 1.21 (3H, t, J=7.1Hz), 1.26 (6H, d, J=6.9Hz), 2.13–2.37 (5H, m), 2.91 (1H, sept, J=6.8Hz), 3.40–4.28 (6H, m), 5.85 (1H, m), 6.14 (1H, s), 7.10–7.35 (6H, m), 7.48 (1H, s) SIMS m/e: 525 (MH$^+$)

TEST EXAMPLE

CRF receptor Binding Assay

The frontal cortical membranes of rats were used as a membrane preparation. [$^{125}$I]-CRF was used as a [$^{125}$I]-labeled ligand.

A binding reaction using a $^{125}$I-labeled ligand was carried out in accordance with the following method described in *The Journal of Neuroscience*, vol. 7, p. 88 (1987).

Membrane preparation:

The rat frontal cortex was homogenized in a 50 mM Tris-HCl buffer (pH7.0) containing 10 mM MgCl$_2$ and 2 mM EDTA, and centrifuged at 48,000×g. The pellet was washed with a Tris-HCl buffer. The pellet was suspended in a 50 mM Tris-HCl buffer (pH 7.0) containing 10 MM MgCl$_2$, 2 mM EDTA, 0.1% bovine serum albumin and 100 kallikrein units/ml-Aprotinin to prepare a membrane preparation. CRF receptor binding assay:

The membrane preparation (0.3 mg-protein/ml), $^{125}$I-CRF (0.2 nM), and a test compound were allowed to react at 25° C. for 2 hours. After completion of the reaction, the reaction mixture was filtered by suction through a glass filter (GF/C) having been treated with 0.3% polyethyleneimine. The glass filter was washed three times with a phosphate-buffered saline solution containing 0.01% Triton X-100, and then the radioactivity of the filter was measured in a gamma counter.

The binding in the presence of 1 μM CRF was taken as a nonspecific binding of $^{125}$I-CRF, and the difference between the total binding and the nonspecific binding was taken as specific binding. $^{125}$I-CRF in a given concentration (0.2 nM) and a test compound in a varied concentration were allowed to react under the above-described conditions to prepare an inhibition curve. The concentration of the test compound which 50% inhibits the $^{125}$I-CRF binding (IC$_{50}$) was obtained from the inhibition curve. The results obtained are shown in Table 3.

TABLE 3

| Compound No. | IC$_{50}$ (nM) |
|---|---|
| 1-01 | 66.08 |
| 1-02 | 22.05 |
| 1-03 | 32.25 |
| 1-05 | 27.59 |
| 1-06 | 10.48 |
| 1-08 | 89.02 |
| 1-12 | 38.54 |
| 1-14 | 73.91 |
| 1-15 | 79.25 |
| 1-16 | 81.11 |
| 1-17 | 73.91 |
| 1-20 | 49.77 |
| 1-21 | 81.11 |
| 1-22 | 89.02 |
| 1-25 | 46.42 |
| 1-26 | 35.11 |
| 1-27 | 12.64 |
| 1-30 | 24.80 |
| 1-31 | 96.18 |
| 1-33 | 55.91 |
| 1-34 | 20.09 |
| 1-36 | 51.51 |
| 1-41 | 38.92 |
| 1-46 | 31.26 |
| 1-51 | 21.54 |
| 1-54 | 65.79 |
| 1-55 | 45.35 |
| 1-57 | 65.79 |
| 1-61 | 67.34 |
| 1-62 | 31.99 |
| 1-66 | 46.42 |
| 1-67 | 61.36 |
| 1-68 | 38.54 |
| 1-71 | 55.91 |
| 1-73 | 65.79 |
| 1-74 | 62.87 |
| 1-77 | 82.36 |
| 1-78 | 52.20 |
| 1-79 | 44.47 |
| 2-01 | 89.02 |
| 2-02 | 96.17 |
| 2-03 | 82.27 |
| 2-04 | 82.27 |
| 2-05 | 27.59 |
| 2-06 | 96.17 |
| 2-07 | 20.19 |
| 2-09 | 97.70 |
| 2-13 | 82.27 |
| 2-15 | 10.81 |

TABLE 3-continued

| Compound No. | IC$_{50}$ (nM) |
| --- | --- |
| 2-18 | 70.38 |
| 2-19 | 70.38 |

INDUSTRIAL APPLICABILITY:

The present invention provides compounds exhibiting high affinity to a CRF receptor. The compounds are effective on diseases which CRF is considered to participate in, such as depression, anxiety, Alzheimer's disease, Parkinson's syndrome, Huntington's chorea, eating disorders, hypertension, digestive diseases, drug dependence, epilepsy, cerebral infarction, cerebral ischemia, cerebral edema, head wounds, inflammation, and immunity-associated diseases.

What is claimed is:

1. A 4-tetrahydropyridylpyrimidine compound represented by formula (I):

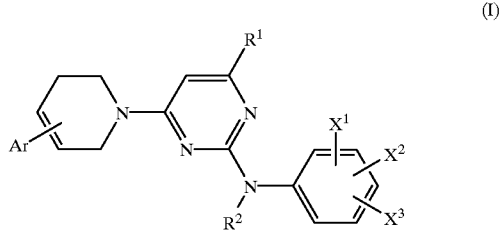

(I)

wherein Ar represents a phenyl group substituted with 1 to 3 substituents selected from a halogen atom, an alkyl group having 1 to 5 carbon atoms, an alkoxy group having 1 to 5 carbon atoms, and a trifluoromethyl group, a phenyl group, a thienyl group or a furanyl group; $R^1$ represents a hydrogen atom, an alkyl group having 1 to 5 carbon atoms, an amino group or an amino group substituted with 1 or 2 alkyl groups having 1 to 5 carbon atoms; $R^2$ represents an alkyl group having 1 to 5 carbon atoms, a cycloalkylalkyl group having 4 to 7 carbon atoms, an alkenyl group having 2 to 5 carbon atoms or an alkynyl group having 2 to 5 carbon atoms; and $X^1$, $X^2$, and $X^3$, which may be the same or different, each represent a hydrogen atom, a halogen atom, an alkyl group having 1 to 5 carbon atoms, an alkoxy group having 1 to 5 carbon atoms, an alkylthio group having 1 to 5 carbon atoms, an amino group or an amino group substituted with 1 or 2 alkyl groups having 1 to 5 carbon atoms, or a pharmaceutically acceptable salt thereof.

2. A 4-tetrahydropyridylpyrimidine compound or a pharmaceutically acceptable salt thereof according to claim 1, wherein, in formula (I), Ar is at the 4-position of the tetrahydropyridine ring and is a phenyl group substituted with 1 to 3 substituents selected from a halogen atom, an alkyl group having 1 to 5 carbon atoms, an alkoxy group having 1 to 5 carbon atoms, and a trifluoromethyl group, a phenyl group, a thienyl group or a furanyl group; $R^1$ is a methyl group; $R^2$ is an ethyl group, a cyclopropylmethyl group, an allyl group or a propargyl group; $X^1$ is a hydrogen atom; $X^2$ is a halogen atom or a methylthio group each bonded at the 2-position of the benzene ring; and $X^3$ is an isopropyl group or a dimethylamino group each bonded at the 4-position of the benzene ring.

3. A tetrahydropyridylpyrimidine compound or a pharmaceutically acceptable salt thereof according to claim 1, wherein, in formula (I), Ar is at the 5-position of the tetrahydropyridine ring and is a phenyl group substituted with 1 to 3 substituents selected from a halogen atom, an alkyl group having 1 to 5 carbon atoms, an alkoxy group having 1 to 5 carbon atoms and a trifluoromethyl group, a phenyl group, a thienyl group or a furanyl group; $R^1$ is a methyl group; $R^2$ is an ethyl group, a cyclopropylmethyl group, an allyl group or a propargyl group; $X^1$ is a hydrogen atom; $X^2$ is a halogen atom or a methylthio group each bonded at the 2-position of the benzene ring; and $X^3$ is an isopropyl group or a dimethylamino group each bonded at the 4-position of the benzene ring.

4. A 4-tetrahydropyridylpyrimidine compound or a pharmaceutically acceptable salt thereof according to claim 2, wherein Ar is a phenyl group substituted with a halogen atom.

5. A 4-tetrahydropyridylpyrimidine compound or a pharmaceutically acceptable salt thereof according to claim 3, wherein Ar is a phenyl group substituted with an alkyl group having 1 to 5 carbon atoms.

6. A CRF receptor antagonist composition comprising the 4-tetrahydropyridylpyrimidine compound or a pharmaceutically acceptable salt thereof according to claim 1 and one or more additives selected from the roup consisting of extenders, binders, disintegrants, pH adjustors, and stabilizers.

* * * * *

UNITED STATES PATENT AND TRADEMARK OFFICE
CERTIFICATE OF CORRECTION

PATENT NO.    : 6,187,781 B1
DATED         : February 13, 2001
INVENTOR(S)   : Nakazato et al.

It is certified that error appears in the above-identified patent and that said Letters Patent is hereby corrected as shown below:

<u>Title page,</u>
Item [54], "4-TETRAHYDROPYRIDYLPYRIMIDINE DERIVATIVES"
should read -- 4-TETRAHYDROPYRIDYLPYRIMIDINE DERIVATIVE --.

Item [86], PCT No.: PCT/JP99/01330" should read -- [86] PCT No.: PCT/JP98/01330 --.

<u>Column 1,</u>
Line 2, "DERIVATIVES" should read -- DERIVATIVE --.

<u>Column 10,</u>
Line 65, "ethylaminol" should read -- ethylamino --.

<u>Columns 13 & 14,</u>
Table 1, line I-20, under the heading "Ar", "3,4-F2-Ph" should read -- 3,4-$F_2$-Ph --;
Line I-21, under the heading "Ar", "3,4-F2-Ph" should read -- 3,4-$F_2$-Ph --;
Line I-22, under the heading "Ar", "3,4-F2-Ph" should read -- 3,4-$F_2$-Ph --;
Line I-23, under the heading "Ar", "3,4-F2-Ph" should read -- 3,4-$F_2$-Ph --;
Line I-24, under the heading "Ar", "3,4-F2-Ph" should read -- 3,4-$F_2$-Ph --;
Line I-25, under the heading "Ar", "3,5-F2-Ph" should read -- 3,5-$F_2$-Ph --;
Line I-26, under the heading "Ar", "3,5-F2-Ph" should read -- 3,5-$F_2$-Ph --;
Line I-27, under the heading "Ar", "3,5-F2-Ph" should read -- 3,5-$F_2$-Ph -- and under the heading "$R^2$", "CH=C-$CH_2$" should read -- CH≡C-$CH_2$ --;
Line I-36, under the heading "$R^2$", "CH=C-$CH_2$" should read -- CH≡C-$CH_2$ --;
Line I-37, under the heading "m.p. (Recry. Sol.$^{*3}$)(°C)", "amorphous$^{*5}$" should read -- amorphous$^{*6}$ --.
Line I-42, under the heading "m.p. (Recry. Sol.*3)(°C)", "1140.0" should read -- 114.0 --;
Line I-45, under the heading "$R^2$", "CH=C-$CH_2$" should read -- CH≡C-$CH_2$ --;
Line I-46, under the heading "$R^2$", "CH=C-$CH_2$" should read -- CH≡C-$CH_2$ --;
Line I-49, under the heading "m.p. (Recry. Sol.$^{*3}$)(°C)", "amorphous$^{*5}$" should read -- amorphous$^{*8}$ --;
Line I-52, under the heading "$R^2$", "CH=C-$CH_2$" should read -- CH≡C-$CH_2$ --;
Line I-63, under the heading "$R^2$", "CH=C-$CH_2$" should read -- CH≡C-$CH_2$ --;
Line I-66, under the heading "Ar", "3-$CF_2$-Ph" should read -- 3-$CF_3$-Ph --;
Line I-67, under the heading "Ar", "3-$CF_2$-Ph" should read -- 3-$CF_3$-Ph -- and under the heading "$X^2$", "4-$Me_2$O" should read -- 4O$Me_2$N --;

UNITED STATES PATENT AND TRADEMARK OFFICE
CERTIFICATE OF CORRECTION

PATENT NO. : 6,187,781 B1  Page 2 of 2
DATED : February 13, 2001
INVENTOR(S) : Nakazato et al.

It is certified that error appears in the above-identified patent and that said Letters Patent is hereby corrected as shown below:

Line I-68, under the heading "Ar", "3-$CF_2$-Ph" should read -- 3-$CF_3$-Ph --;
Line I-69, under the heading "Ar", "3-$CF_2$-Ph" should read -- 3-$CF_3$-Ph -- and under the heading "$R^2$", "CH=C-$CH_2$" should read -- CH≡C-$CH_2$ --;
Line I-70, under the heading "Ar", "3-$CF_2$-Ph" should read -- 3-$CF_3$-Ph --; and
Line I-71, under the heading "Ar", "3-$CF_2$-Ph" should read -- 3-$CF_3$-Ph --;

Columns 15 & 16,
Line 2, of Note "*5", "j=", each instance, should read -- J= --; and line 2 of Note "*12", "15.79" should read -- 5.79 -- and "J=3.31" should read -- J=3.3 --.

Column 16,
Line 59, "4-(5-phenyl-1 2,3, 6-tetrahydropyridin-1-yl)" should read -- "4-(5-phenyl-1,2,3, 6-tetrahydropyridin-1-yl) --.

Column 18,
Table 2, line 2-07, under the heading "R2", "CH=C-CH2" should read -- CH≡C-$CH_2$ --.

Column 19,
Table 2, before the line reading "IPA; isopropyl alcohol", insert a line reading -- $Et_2O$: diethyl ether --.

Signed and Sealed this

Tenth Day of September, 2002

Attest:

JAMES E. ROGAN
Attesting Officer    Director of the United States Patent and Trademark Office